United States Patent
Conza et al.

(10) Patent No.: US 9,701,688 B2
(45) Date of Patent: Jul. 11, 2017

(54) PROCESS FOR THE PREPARATION OF OPIOID COMPOUNDS

(71) Applicant: NORAMCO, INC., Athens, GA (US)

(72) Inventors: Matteo Conza, Schaffhausen (CH); Vit Lellek, Eglisau (CH); Hartmut Zinser, Schaffhausen (CH)

(73) Assignee: NORAMCO, INC., Athens, GA (US)

( * ) Notice: Subject to any disclaimer, the term of this patent is extended or adjusted under 35 U.S.C. 154(b) by 0 days.

(21) Appl. No.: 14/689,712

(22) Filed: Apr. 17, 2015

(65) Prior Publication Data

US 2015/0315205 A1    Nov. 5, 2015

Related U.S. Application Data

(60) Provisional application No. 61/988,523, filed on May 5, 2014.

(51) Int. Cl.
*C07D 489/12*    (2006.01)
*C07D 489/08*    (2006.01)

(52) U.S. Cl.
CPC ......... *C07D 489/12* (2013.01); *C07D 489/08* (2013.01)

(58) Field of Classification Search
USPC ........................................................ 546/39
See application file for complete search history.

(56) References Cited

U.S. PATENT DOCUMENTS

| | | | |
|---|---|---|---|
| 3,433,791 A | 3/1969 | Bently | |
| 8,080,661 B2 | 12/2011 | Wang et al. | |
| 8,227,608 B2 | 7/2012 | Allen | |
| 8,232,398 B2 | 7/2012 | Kalota | |
| 8,236,957 B2 | 8/2012 | Rezaie et al. | |
| 8,273,887 B2 | 9/2012 | Mannino et al. | |
| 8,273,889 B2 | 9/2012 | Hamada et al. | |
| 8,293,906 B2 | 10/2012 | Jarvi et al. | |
| 2008/0125592 A1 | 5/2008 | Huang | |
| 2010/0210843 A1 | 8/2010 | Hudson et al. | |
| 2011/0313163 A1 | 12/2011 | Hudlicky et al. | |
| 2012/0046465 A1 | 2/2012 | Hudlicky et al. | |
| 2012/0156290 A1 | 6/2012 | Huang | |
| 2012/0283443 A1 | 11/2012 | Hudlicky et al. | |

FOREIGN PATENT DOCUMENTS

| | | |
|---|---|---|
| WO | WO 2008/064351 A2 | 5/2008 |
| WO | WO 2008/137672 A1 | 11/2008 |
| WO | WO 2013/050748 A2 | 4/2013 |
| WO | 2013/113120 A1 | 8/2013 |
| WO | WO 2013/113120 A1 | 8/2013 |

OTHER PUBLICATIONS

International Search Report dated Jan. 28, 2016, International Application No. PCT/US2015/027906.

Machara et al., entitled "Improved Synthesis of Buprenorphine from Thebaine and/or Oripavine via Palladium-Catalyzed N-Demethylation/Acylation and/or Concomitant O-Demethylation". Advanced Synthesis and Catalysis, Wiley Weinheim, DE, vol. 354, No. 4; Jan. 1, 2012, pp. 613-626. XP009177295, ISSN: 1615-4169 scheme 2, compound 8 to compound 1; p. 622.

International Search Report dated Aug. 10, 2015, International Application No. PCT/US2015/027912.

*Primary Examiner* — Charanjit Aulakh
(74) *Attorney, Agent, or Firm* — Morgan, Lewis & Bockius LLP

(57) ABSTRACT

The present invention is directed to a process for the preparation of opioid compounds such as buprenorphine, naltrexone, naloxone, nalbuphone, nalbuphine, and the like.

24 Claims, No Drawings

PROCESS FOR THE PREPARATION OF OPIOID COMPOUNDS

CROSS REFERENCE TO RELATED APPLICATIONS

This application claims the benefit of U.S. Provisional Application 61/988,523, filed on May 5, 2015, which is incorporated by reference herein in its entirety.

FIELD OF THE INVENTION

The present invention is directed to a process for the preparation of opioid compounds such as buprenorphine, naltrexone, naloxone, nalbuphone, nalbuphine, and the like.

BACKGROUND OF THE INVENTION

Buprenorphine is a semi-synthetic opioid derivative of thebaine that is used to treat opioid addiction in higher dosages (>2 mg), to control moderate acute pain in non-opioid-tolerant individuals in lower dosages (~200 μg), and to control moderate chronic pain in dosages ranging from 20-70 μg/hour. It is available in a variety of formulations: SUBUTEX, SUBOXONE, ZUBSOLV (buprenorphine HCl and naloxine HCl; typically used for opioid addiction), TEMGESIC (sublingual tablets for moderate to severe pain), BUPRENEX (solutions for injection often used for acute pain in primary-care settings), NORSPAN and BUTRANS (transdermal preparations used for chronic pain).

As an opioid, buprenorphine lends itself to some uses for which it has not been approved by the drug regulatory agency of the country in which it is used (such as the U.S. FDA). One such off-label use (perhaps the most common) is the use of SUBUTEX or SUBOXONE, a formulation intended solely for the treatment of opioid abuse, in palliation of severe pain with no neuralgic component or when the neuralgia is otherwise treated, such as with pregabalin. Niche pain indications for which SUBUTEX or SUBOXONE may be a medication of choice include obstruction of the small bowel; continuous nasogastric suction; oesophageal fistula; malignancy in the head or neck; and other cases where the patient is unable to swallow or this is difficult. Additionally, SUBUTEX or SUBOXONE may be an interesting alternative to sustained-release opioids such as morphine (MS CONTIN) and oxycodone (TARGIN).

Furthermore, buprenorphine is somewhat sleep-inducing, and may be of particular help when pain leads to sleeplessness. Other prototypical opioid side-effects may prove beneficial in the management of chronic pain, such as its characteristic euphoria (to alleviate depression due to pain, or in cases where the patient cannot tolerate or is resistant to conventional thymoleptic antidepressants), as well as its anxiolytic effects. These effects manifest themselves chiefly when buprenorphine is used in patients not tolerant to opioids; use of a partial agonist such as buprenorphine in those tolerant or dependent will simply lead to precipitated withdrawal (if a different opioid is used concomitantly) or relief of withdrawal (if used as monotherapy).

Naltrexone is an opioid receptor antagonist used primarily in the management of alcohol dependence and opioid dependence. The main use of naltrexone is for the treatment of alcohol dependence. It is marketed in generic form as its hydrochloride salt, naltrexone hydrochloride, and marketed under the trade names REVIA and DEPADE. In some countries including the United States, a once-monthly extended-release injectable formulation is marketed under the trade name VIVITROL.

Naloxone is an opioid antagonist used to counter the effects of opiate overdose, for example heroin or morphine. Naloxone is specifically used to counteract life-threatening depression of the central nervous system and respiratory system. Naloxone is also experimentally used in the treatment of congenital insensitivity to pain with anhidrosis (CIPA), an extremely rare disorder (1 in 125 million) that renders one unable to feel pain, or differentiate temperatures. Naloxone is marketed under various trademarks including NARCAN, NALONE and NARCANTI.

Nalbuphine is a semi-synthetic opioid, available under the trade name of NUBAIN for the treatment of moderate to severe pain. It can also be used as a supplement to balanced anesthesia, for preoperative and postoperative analgesia, and for obstetrical analgesia during labor and deliver. Nalbuphine is a semi-synthetic opioid agonist-antagonist analgesic of the phenanthrene series, and is chemically related to the widely used opioid antagonists, naloxone and naltrexone, and the potent opioid analgesic, oxymorphone.

HAMADA, T., et a., in U.S. Pat. No. 8,273,889 B2, issued Sep. 25, 2012 disclose a method for producing 2-azaadamantane, which process includes cyclizing in the presence of an acid.

KALOTA, D. J., in U.S. Pat. No. 8,232,398 B2, issued Jul. 31, 2012 discloses a recycling process for increasing the yield of opiate alkaloid derivatives, by introducing at least one recycling step.

WANG, P. X., et al., in U.S. Pat. No. 8,080,661 B2, issued Dec. 20, 2011 disclose processes for the synthesis of tertiary amines by directed N-alkylation, co-mediated by an alkylating agent and a protic solvent or a mixture of a protic solvent and an aprotic solvent.

ALLEN, B. E., in U.S. Pat. No. 8,227,608 B2, issued Jul. 24, 2012 discloses processes for increasing the yield of opiate alkaloid derivatives.

JARVI, E. T., et al., in U.S. Pat. No. 8,293,906 B2, issued Oct. 23, 2013 disclose processes for the alkylation of norbuprenorphine with reduced impurity formation.

BENTLEY, K. W., in U.S. Pat. No. 3,433,791, issued Mar. 18, 1969 discloses endoethano nor-oripavines and nor-thebanes.

HUDSON, E. G., et al., in US Patent Publication 2010/0210843 A1, published Aug. 19, 2010 disclose a process for the reductive alkylation of normorphinans by a carboxaldehyde in the presence of a reducing agent.

HUANG, B-S. in US Patent Publication 2008/0125592 A1, published May 29, 2008 discloses a process for preparing oxymorphone, naltrexone and buprenorphine.

HUANG, B-S., in US Patent Publication 2012/0156290 A1, published Jun. 21, 2012 discloses a process for preparing oxymorphone, naltrexone, and buprenorphine.

ARCHER, N., et al., in PCT Publication WO 2013/050748 A2, published Apr. 11, 2013 disclose a process for preparing buprenorphine, comprising O-demthylation followed by N-alkylation with cyclopropylmethyl bromide.

There remains a need for a process for the preparation of opioids which is suitable for large scale/commercial manufacture, preferably a process which has fewer steps and/or fewer distillations and/or fewer isolation steps than current processes; while maintaining high yields and/or high purity in the final product.

SUMMARY OF THE INVENTION

The present invention is directed to a process for the preparation of opioid compounds, opioid derivatives, and pharmaceutically acceptable salts thereof. More particularly, the present invention is directed to processes comprising N-alkylation in the presence of an inorganic base, wherein the inorganic base is selected to be a base which does not form water when reacted with or contacted with an acid; and wherein the inorganic base is preferably selected to be a base which selectively, does not protonate free phenol group(s) (i.e. a phenolic OH group(s)), if present; followed by optional de-methylation, preferably without isolation of the N-alkylated intermediate.

In an embodiment, the present invention is directed to a process for the preparation of a compound of formula (I)

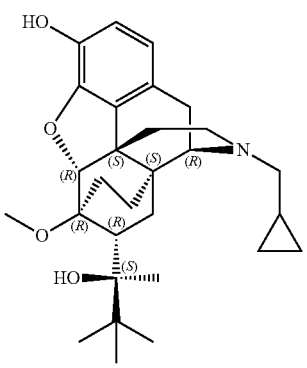

(I)

or a pharmaceutically acceptable salt thereof; comprising

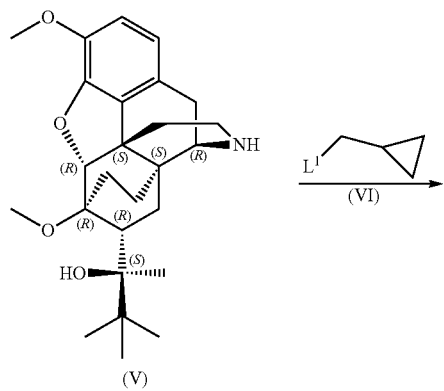

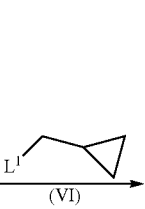

reacting a compound of formula (V) with a compound of formula (VI), wherein $L^1$ is a leaving group; in the presence of an inorganic base; wherein the inorganic base does not form water when reacted with or contacted with an acid; in a first organic solvent; at a temperature in the range of from about 40° C. to about 70° C.; to yield the corresponding compound of formula (VII); and

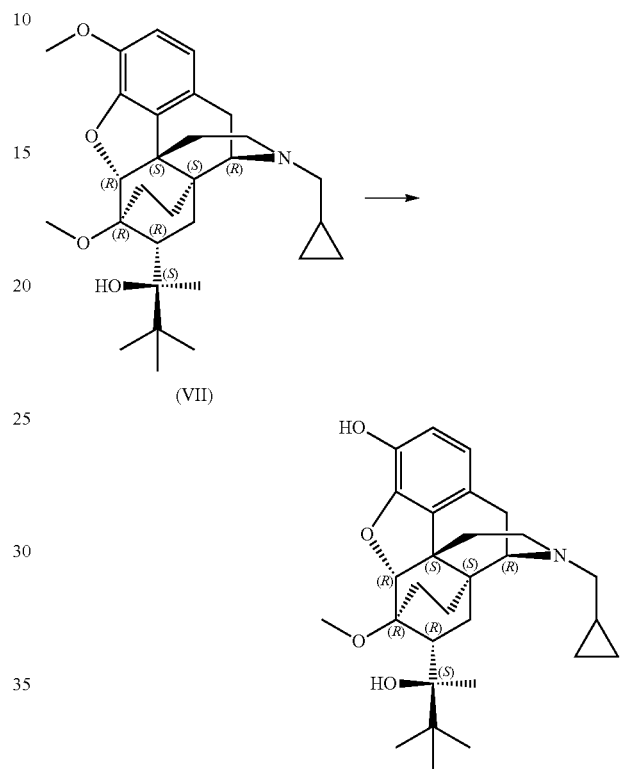

(VII)

(I)

reacting the compound of formula (VII) with a demethylating agent (preferably an O-demethylating agent); in the presence of a base; in a second organic solvent; at a temperature in the range of from about 110° C. to about 150° C.; under an inert atmosphere; to yield the corresponding compound of formula (I).

The present invention is further directed to a process for the preparation of a compound of formula (I)

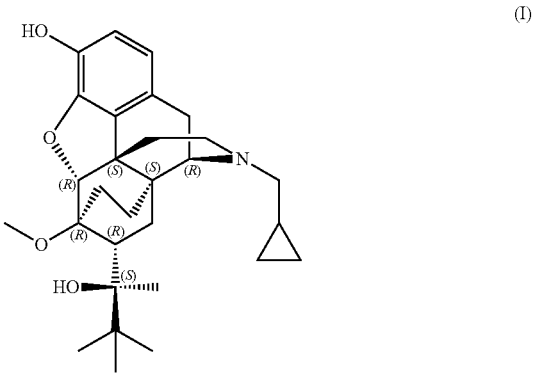

(I)

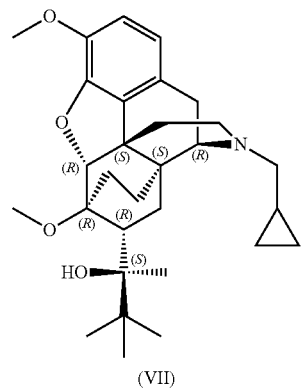

(VII)

or a pharmaceutically acceptable salt thereof; comprising

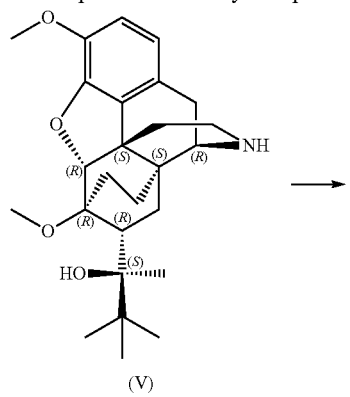

(V)

reacting a formula (V), with a demethylating agent (preferably an O-demethylating agent); in the presence of a base; in a first organic solvent; at a temperature in the range of from about 110° C. to about 150° C.; under an inert atmosphere; to yield the corresponding compound of formula (VIII);

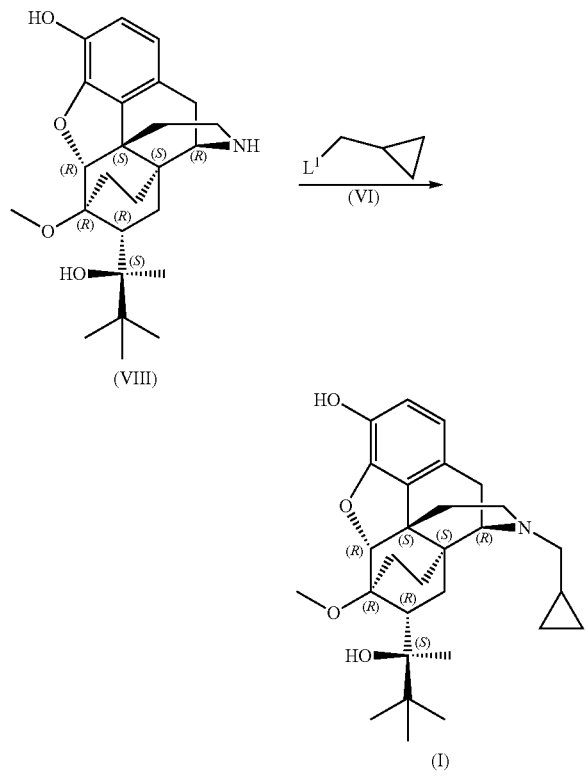

reacting the compound of formula (VIII) with a compound of formula (VI), wherein $L^1$ is a leaving group; in the presence of an inorganic base; wherein the inorganic base does not form water when reacted with or contacted with an acid, and wherein the inorganic base is preferably a base which selectively does not protonate the free phenol (i.e. the phenolic OH group) on the compound of formula (VIII); in a second organic solvent; at a temperature in the range of from about 40° C. to about 70° C.; to yield the corresponding compound of formula (I).

In another embodiment, the present invention is directed to a process for the preparation of a compound of formula (II)

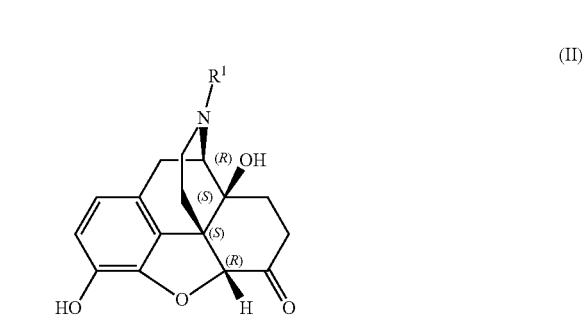

wherein $R^1$ is selected from the group consisting of —$CH_2$-(cyclopropyl), —$CH_2$-(cyclobutyl) and —$CH_2$—$CH$=$CH_2$; or a pharmaceutically acceptable salt thereof, comprising

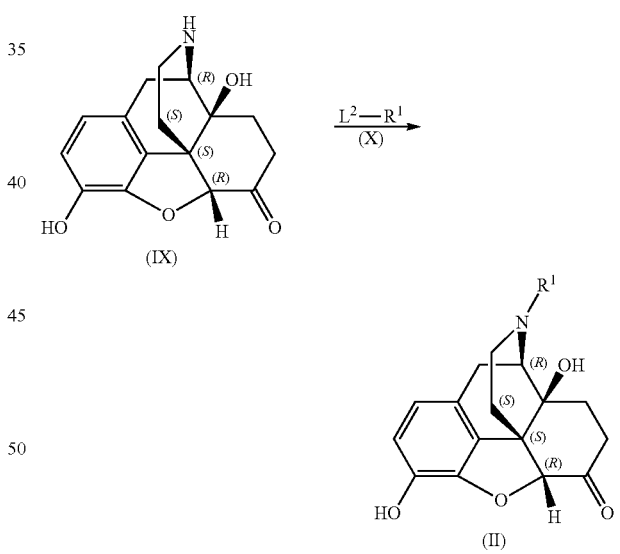

reacting a compound of formula (IX) with a compound of formula (X), wherein $L^2$ is a leaving group; in the presence of an inorganic base; wherein the inorganic base does not form water when reacted with or contacted with an acid; and wherein the inorganic base is preferably selected to be a base which selectively, does not protonate the free phenol (i.e. the phenolic OH group) on the compound of formula (IX); in a first organic solvent; at a temperature in the range of from about 40° C. to about 70° C.; to yield the corresponding compound of formula (II).

In an embodiment of the present invention, the compound of formula (II) is a compound of formula (IIa)

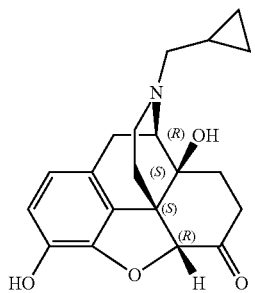

(also known as naltrexone; wherein $R^1$ is —$CH_2$-(cyclopropyl)) or a pharmaceutically acceptable salt thereof. In another embodiment of the present invention, the compound of formula (II) is a compound of formula (IIb)

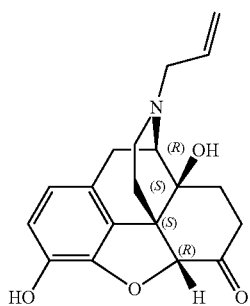

(also known as naloxone; wherein $R^1$ is —$CH_2$—$CH{=}CH_2$) or a pharmaceutically acceptable salt thereof. In another embodiment of the present invention, the compound of formula (II) is a compound of formula (IIc)

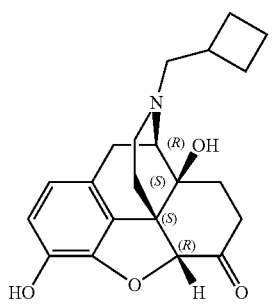

(also known as nalbuphone; wherein $R^1$ is —$CH_2$-(cyclobutyl)) or a pharmaceutically acceptable salt thereof.

The present invention is further directed to a product prepared according to any of the processes described herein.

Illustrative of the invention is a pharmaceutical composition comprising a pharmaceutically acceptable carrier and a product prepared according to any of the processes described herein. An illustration of the invention is a pharmaceutical composition made by mixing a product prepared according to any of the processes described herein and a pharmaceutically acceptable carrier. Illustrating the invention is a process for making a pharmaceutical composition comprising mixing a product prepared according to any of the processes described herein and a pharmaceutically acceptable carrier.

Exemplifying the invention are methods for the treatment of pain (for example moderate or severe pain) comprising administering to a subject in need thereof a therapeutically effective amount of any of the products or pharmaceutical compositions described above.

In an embodiment, the present invention is directed to a product prepared according to any of the processes described herein for use as a medicament. In another embodiment, the present invention is directed to a product prepared according to any of the processes described herein for use in the treatment pain (for example moderate or severe pain). In another embodiment, the present invention is directed to a composition comprising a product prepared according to any of the processes described herein for the treatment of pain (for example moderate or severe pain).

Another example of the invention is the use of a product prepared according to any of the processes described herein in the preparation of a medicament for treating pain (for example moderate or severe pain), in a subject in need thereof. In another example, the present invention is directed to a product prepared according to any of the processes described herein for use in a methods for treating pain (for example moderate or severe pain), in a subject in need thereof.

DETAILED DESCRIPTION OF THE INVENTION

The present invention is directed to a process for the preparation of opioid compounds, more particularly compounds of formula (I)

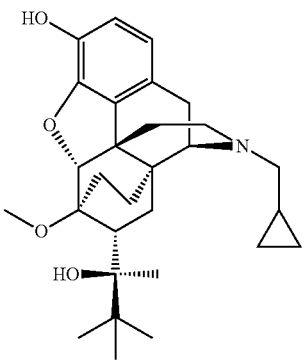

and pharmaceutically acceptable salt thereof; and compounds of formula (II)

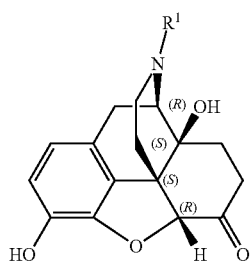

wherein $R^1$ is selected from the group consisting of —$CH_2$-(cyclopropyl), —$CH_2$-(cyclobutyl) and —$CH_2$—

CH=CH$_2$, and pharmaceutically acceptable salts thereof. The compounds of formula (I), the compounds of formula (II), and pharmaceutically acceptable salts thereof, are useful for the treatment of pain, including acute and chronic pain (for example moderate or severe pain), opioid addiction, alcohol addiction, opioid detoxification and/or for counteracting opioid overdose; or are useful as intermediates in the synthesis of compounds useful for the treatment of pain.

Abbreviations used in the specification, particularly the Schemes and Examples, are as follows:
CPMB=Cyclopropylmethyl bromide
CPS Thebaine=Concentrate of poppy straw, thebaine
CsNEt$_2$=Cesium Diethylamide
CsOEt=Cesium Ethoxide
CsOtBu or CsOt-Bu=Cesium tert-Butoxide
DCM=Dichloromethane
DMA=Dimethylacetamide
DMF=N,N-Dimethylformamide
DMI=1,3-Dimethyl-2-imidazolidinone
DMSO=Dimethyl sulfoxide
HPLC=High Performance Liquid Chromatography
IPC=In-Process Control
KDA=Potassium diisopropylamide
KHMDS=Potassium bis(trimethylsilyl)amide
KOEt=Potassium Ethoxide
KOtBu or KOt-Bu=Potassium tert-Butoxide
LDA=Lithium diisopropylamide
LiHMDS=Lithium bis(trimethylsilyl)amide
LiNEt$_2$=Lithium diethylamide
LiOEt=Lithium Ethoxide
LiOtBu or LiOt-Bu=Lithium tert-Butoxide
Mesyl=Methylsulfonyl
MOM=Methoxymethyl ether
n-BuLi=n-Butyl Lithium
NaNEt$_2$=Sodium Diethylamide
NaOEt=Sodium Ethoxide
NaOtBu or NaOt-Bu=Sodium tert-Butoxide
NMP=N-methyl-2-pyrrolidone
NOMO=Noroxymorphone
Pd—C or Pd/C=Palladium on Carbon Catalyst
t-Bu or tert-Bu=tert-Butyl
tert-BuMgCl=tert-Butyl magnesium chloride
THF=Tetrahydrofuran
THP=Tetrahydropyranyl
TMS=Trimethylsilyl
Tosyl=p-Toluenesulfonyl As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

It is intended that within the scope of the present invention, any element, in particular when mentioned in relation to a compound of formula (I) or a compound of formula (II), shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$O, $^{13}$O and $^{14}$O and $^{16}$O and $^{18}$O. The isotopes may be radioactive or non-radioactive. Radiolabelled compounds of formula (I) or formula (II) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br, and $^{82}$Br. Preferably, the radioactive isotope is selected from the group of $^3$H, $^{11}$C and $^{18}$F.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment, the present invention is directed to a process wherein the compound of formula (I) is prepared as a substantially pure form. In another embodiment, the present invention is directed to a process wherein the compound of formula (II) is prepared as a substantially pure form.

As used herein, unless otherwise noted, the term "substantially free of a corresponding salt form(s)" when used to described the compound of formula (I) or formula (II) shall mean that mole percent of the corresponding salt form(s) in the isolated base of formula (I) or isolated base of formula (II) is less than about 5 mole percent, preferably less than about 2 mole percent, more preferably, less than about 0.5 mole percent, most preferably less than about 0.1 mole percent. In an embodiment, the present invention is directed to a process wherein the compound of formula (I) is prepared in a form which is substantially free of corresponding salt form(s). In another embodiment, the present invention is directed to a process wherein the compound of formula (II) is prepared in a form which is substantially free of corresponding salt form(s).

As used herein, unless otherwise noted, the terms "treating", "treatment" and the like, shall include the management and care of a subject or patient (preferably a mammal, more preferably a human) for the purpose of combating a disease, condition, or disorder and includes the administration of a compound or product of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an inorganic base as a reagent, the inorganic base selected for the first step may be the same or different than the inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

Examples of suitable solvents, bases, reaction temperatures, and other reaction parameters and components are provided in the detailed description which follows herein. One skilled in the art will recognize that the listing of said examples is not intended, and should not be construed, as limiting in any way the invention set forth in the claims which follow thereafter.

As used herein, unless otherwise noted, the term "dipolar aprotic solvent" shall mean an organic solvent with characteristically high polarity and low reactivity, that is, a solvent having a sizable permanent dipole moment that cannot donate labile hydrogen atoms to form strong hydrogen bonds. Suitable examples include, but are not limited to dimethylformamide (DMF), dimethylacetamide (DMA), N-methylpyrrolidinone (NMP), dimethylsulfoxide (DMSO), sulfolane, 1,3-dimethyl-2-imidazolidinone (DMI), dialklylamide solvents, and the like.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, triflate, nosylate, nonaflate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to an oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α−obs]/[α−max])×100.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The present invention is directed to a process for the preparation of opioid compounds of formula (I) and formula (II), and pharmaceutically acceptable salts thereof, as herein defined, comprising N-alkylation with a suitably selected alkylating agent (for example an alkylhalide);

in the presence of a suitably selected inorganic base, preferably an anhydrous inorganic base; wherein the inorganic base does not form water when reacted with or contacted with an acid, and wherein the inorganic base is sufficiently strong to neutralize any acid formed as a by-product of the reaction with the alkylating agent (for example, HBr which is formed as a by-product of the reaction with cyclopropylmethyl bromide), such as $K_2HPO_4$, $K_3PO_4$, $LiH_2PO_4$, $NaH_2PO_4$, $KH_2PO_4$, $CsH_2PO_4$, $Li_2HPO_4$, $Na_2HPO_4$, $K_2HPO_4$, $Cs_2HPO_4$, $Li_3PO_4$, $Na_3PO_4$, $K_3PO_4$, $Cs_3PO_4$, $Ca((H_2PO_4)_2$, $Ba(H_2PO_4)_2$, $Ca(HPO_4)$, $Ba(HPO_4)$, $Ca_3(PO_4)_3$, $Ba_3(PO_4)_3$, and the like, preferably anhydrous $K_2HPO_4$ or anhydrous $K_3PO_4$, more preferably anhydrous $K_2HPO_4$; wherein the inorganic base is preferably present in an amount greater than about 1 molar equivalent, preferably in an amount in the range of from about 1.5 to about 5 molar equivalents, preferably in an amount in the range of from about 2 to about 4 molar equivalents; preferably in an amount in the range of from about 2.25 to about 3.25 molar equivalents, preferably in an amount in the range of from about 2.4 to about 3 molar equivalents;

optionally in the presence of a promoter such as NaI, NaBr, tetralkylammonium iodide (such as tetra(n-butyl) ammonium iodide, and the like), tetralkylammonium bromide (such as tetra(n-butyl)ammonium bromide, and the like), triethylbenzylammonium iodide, triethylbenzylammonium bromide, and the like; wherein the promoter is present in an amount in the range of from about 1 mole % to about 10 mole %, preferably in an amount in the range of from about 5 mole % to about 10 mole %;

in a suitably selected first organic solvent (for example a dipolar aprotic solvent) such as DMF, DMA, NMP, DMSO, sulfolane, DMI, and the like, preferably DMF; at a temperature in the range of from about 40° C. to about 70° C., preferably at a temperature in the range of from about 55° C. to about 65° C., more preferably at a temperature of about 60° C.

In the processes of the present invention, the inorganic base is selected to be a base which does not produce water as a by-product of the alkylation reaction (i.e. an inorganic base which does not produce water when reacted with or contacted with an acid). Advantageously, the absence of water in the product mixture resulting from the N-alkylation, eliminates the need for a distillation step following the N-alkylation (and before any optional 0-demethylation step).

In the processes of the present invention, the inorganic base is selected to be a base which can neutralize any acid produced as a by-product of the N-alkylation. For example, wherein the N-alkylation is achieved by reacting with a suitably substituted alkylbromide, the inorganic base is selected to be a base which is capable of neutralizing any HBr produced as a by-product of said reaction.

In an embodiment, the present invention is directed to a process for the preparation of a compound of formula (I) or a pharmaceutically acceptable salt thereof, as described in Scheme 1 below.

Scheme 1

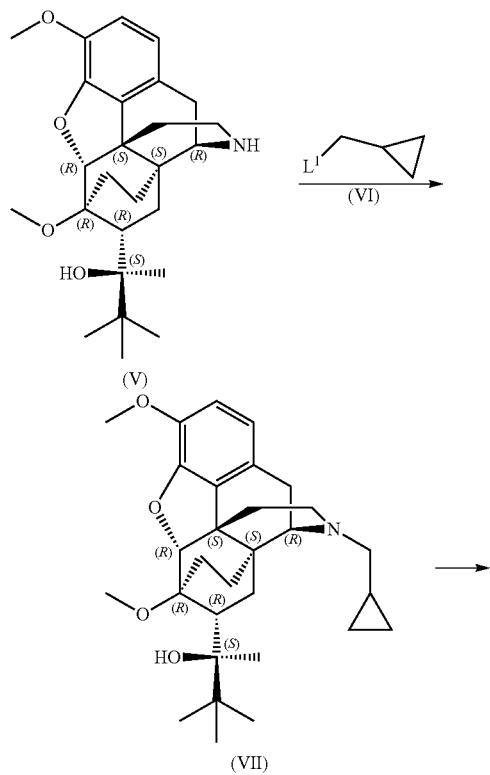

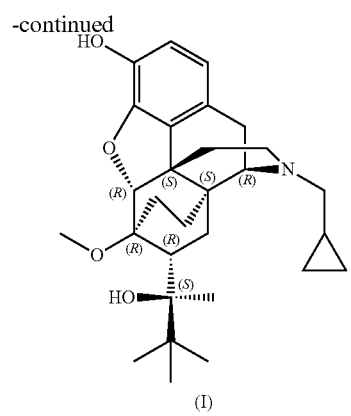

(I)

Accordingly, a suitably substituted compound of formula (V), a known compound or compound prepared by known methods (for example as described in Example 1 which follows herein), is reacted with a suitably substituted compound of formula (VI), wherein $L^1$ is a suitably selected leaving group such as Br, Cl, I, mesylate, tosylate, nosylate, triflate, nonaflate, and the like, preferably Br, a known compound or compound prepared by known methods; wherein the compound of formula (VI) is preferably present in an amount greater than about 1 molar equivalent (relative to the moles of the compound of formula (V)), preferably in an amount in the range of from about 1.1 to about 2.5 molar equivalents, preferably in an amount in the range of from about 1.25 to about 1.75 molar equivalents, preferably in an amount in the range of from about 1.3 to about 1.5 molar equivalents, more preferably in an amount of about 1.4 molar equivalents;

in the presence of a suitably selected inorganic base, preferably an anhydrous inorganic base; wherein the inorganic base does not form water when reacted with or contacted with an acid, and wherein the inorganic base is sufficiently strong to neutralize any acid formed as a by-product of the reaction with the alkylating agent (for example, HBr which is formed as a by-product of the reaction with cyclopropylmethyl bromide), such as $K_2HPO_4$, $K_3PO_4$, $LiH_2PO_4$, $NaH_2PO_4$, $KH_2PO_4$, $CsH_2PO_4$, $Li_2HPO_4$, $Na_2HPO_4$, $K_2HPO_4$, $Cs_2HPO_4$, $Li_3PO_4$, $Na_3PO_4$, $K_3PO_4$, $Cs_3PO_4$, $Ca((H_2PO_4)_2$, $Ba(H_2PO_4)_2$, $Ca(HPO_4)_3$, $Ba(HPO_4)$, $Ca(PO_4)_3$, $Ba(PO_4)_3$, and the like, preferably anhydrous $K_2HPO_4$ or anhydrous $K_3PO_4$, more preferably anhydrous $K_2HPO_4$; wherein the inorganic base is preferably present in an amount greater than about 1 molar equivalent (relative to the moles of the compound of formula (V)), preferably in an amount in the range of from about 1.5 to about 5 molar equivalents (relative to the moles of the compound of formula (V)), preferably in an amount in the range of from about 2 to about 4 molar equivalents; preferably in an amount in the range of from about 2.25 to about 3.25 molar equivalents, preferably in an amount in the range of from about 2.4 to about 3 molar equivalents;

optionally in the presence of a promoter such as NaI, NaBr, tetralkylammonium iodide (such as tetra(n-butyl) ammonium iodide, and the like), tetralkylammonium bromide (such as tetra(n-butyl)ammonium bromide, and the like), triethylbenzylammonium iodide, triethylbenzylammonium bromide, and the like; wherein the promoter is present in an amount in the range of from about 1 mole % to about 10 mole %, preferably in an amount in the range of from about 5 mole % to about 10 mole %;

in a suitably selected first organic solvent (for example a dipolar aprotic solvent) such as DMF, DMA, NMP, DMSO, sulfolane, DMI, and the like, preferably DMF; at a temperature in the range of from about 40° C. to about 70° C., preferably at a temperature in the range of from about 55° C. to about 65° C., more preferably at a temperature of about 60° C.; to yield the corresponding compound of formula (VII).

The compound of formula (VII) is preferably not isolated.

In an embodiment of the present invention, the reaction mixture containing the compound of formula (V), the inorganic base and the first organic solvent has a total water content of less than about 1% w/w, more preferably less than about 0.75% w/w, more preferably less than about 0.60% w/w, more preferably less than about 0.50% w/w.

One skilled in the art will recognize that in the reaction of the compound of formula (V) with the compound of formula (VI), the $L^1$ group from the compound of formula (VI) reacts with the hydrogen released from the compound of formula (V) to produce an acid as a by-product (for example, wherein the $L^1$ is bromo, the acid produced as a by-product of the reaction is HBr). One skilled in the art will further recognize that said acid is neutralized by the suitably selected inorganic base, to yield the corresponding salt. In the processes of the present invention, the product mixture resulting from the reaction of the compound of formula (V) with the compound of formula (VI) is optionally filtered to remove the salt resulting from the neutralization of the acid and further to remove any residual base.

The compound of formula (VII) is reacted with a suitably selected demethylating agent, preferably an O-demethylating agent (for example, a suitably selected mercaptan) such as n-$C_6$SH (n-hexane thiol), n-$C_7$SH (n-heptane thiol), n-$C_8$SH (n-octane thiol), n-$C_9$SH (n-nonane thiol, n-$C_{10}$SH (n-decane thiol), n-$C_{11}$SH, (n-undecane thiol), n-$C_{12}$SH (n-docecane thiol), t-$C_4$SH (tert-butylmercaptan or 2-methyl-propane thiol), t-$C_6$SH (2-methylpentane-2-thiol), t-$C_7$SH (2-methylhexane-2-thiol), t-$C_8$SH (2-methylheptane-2-thiol), t-$C_9$SH (2-methyloctane-2-thiol), t-$C_{10}$SH (tert-decanethiol), t-$C_{11}$SH (2-methyldecane-2-thiol), t-$C_{12}$SH (tert-dodecyl mercaptan or 2-methylundecane thiol), and the like (for example, other commercially available thio demethylating agents), preferably tert-dodecyl mercaptan; wherein the demethylating agent is preferably present in an amount in the range of from about 2 to about 5 molar equivalents (relative to the moles of the compound of formula (V)), preferably in an amount in the range of from about 2.5 to about 4 molar equivalents; more preferably in an amount in the range of from about 2.8 to about 3.4 molar equivalents, more preferably in an amount of about 3.1 molar equivalents;

in the presence of a suitably selected base such as a suitably selected inorganic alcohol such as NaOH, KOH, LiOH, CsOH, and the like or a suitably selected alkoxide base such as NaOEt, NaOtBu, KOEt, KOtBu, LiOEt, LiOtBu, CsOEt, CsOtBu, and the like; or a suitably selected amine base such as LiNEt$_2$, NaNEt$_2$, CsNEt$_2$, LiNH$_2$, NaNH$_2$, CsNH$_2$, and the like, or a suitably selected hydride base such as NaH, KH, CsH, and the like, or a suitably selected base such as LDA, KDA, LiHMDS, KHMDS, n-BuLi, and the like; preferably NaOtBu; wherein the base is preferably present in an amount in the range of from about 2 to about 5 molar equivalents (relative to the moles of the compound of formula (V), preferably in an amount in the range of from about 2.5 to about 4 molar equivalents; more preferably in an amount in the range of from about 2.8 to about 3.4 molar equivalents, more preferably in an amount of about 3.1 molar equivalents;

in a suitably selected second organic solvent (for example a dipolar aprotic solvent) such as DMF, DMA, NMP, DMSO, sulfolane, DMI, and the like, preferably DMF; wherein the second organic solvent is preferably the same as the first organic solvent; at a temperature in the range of from about 110° C. to about 150° C., preferably at a temperature in the range of 128° C. to about 135° C., more preferably at a temperature of about 131° C.; under an inert atmosphere, such as under nitrogen, under argon, under helium, and the like; to yield the corresponding compound of formula (I).

In another embodiment, the present invention is directed to a process for the preparation of a compound of formula (I) or a pharmaceutically acceptable salt thereof, as described in Scheme 2, below.

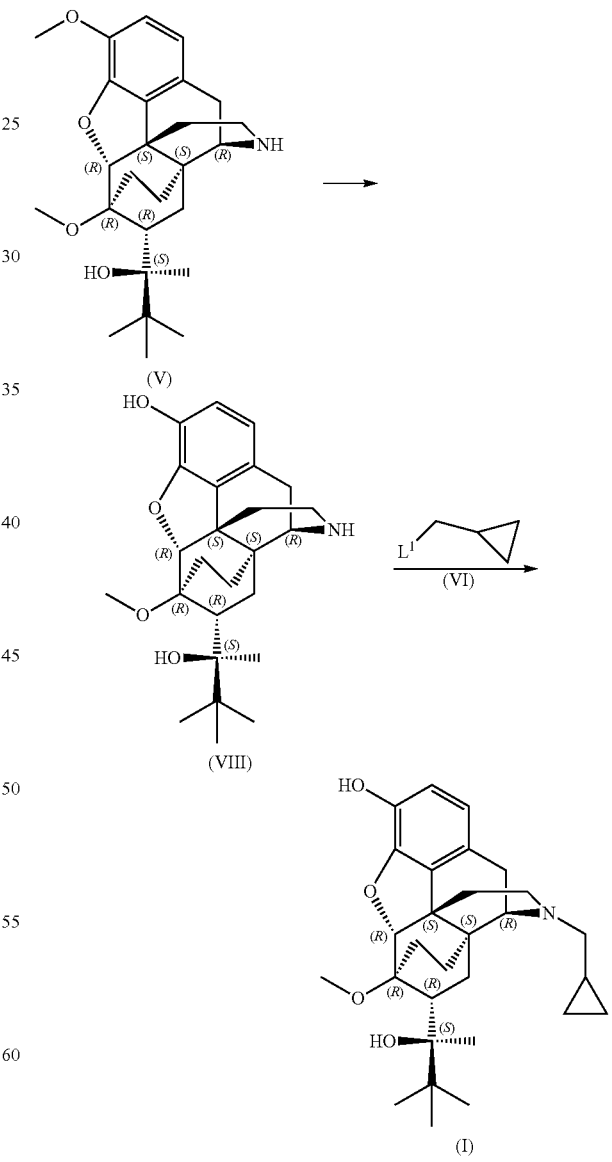

Scheme 2

Accordingly, a suitably substituted compound of formula (V), a known compound or compound prepared by known methods, is reacted with a suitably selected demethylating agent, preferably an O-demethylating agent (for example, a suitably selected mercaptan) such as n-$C_6$SH (n-hexane thiol), n-$C_7$SH (n-heptane thiol), n-$C_8$SH (n-octane thiol), n-$C_9$SH (n-nonane thiol, n-$C_{10}$SH (n-decane thiol), n-$C_{11}$SH, (n-undecane thiol), n-$C_{12}$SH (n-docecane thiol), t-$C_4$SH (tert-butylmercaptan or 2-methyl-propane thiol), t-$C_6$SH (2-methylpentane-2-thiol), t-$C_7$SH (2-methylhexane-2-thiol), t-$C_8$SH (2-methylheptane-2-thiol), t-$C_9$SH (2-methyloctane-2-thiol), t-$C_{10}$SH (tert-decanethiol), t-$C_{11}$SH (2-methyldecane-2-thiol), t-$C_{12}$SH (tert-dodecyl mercaptan or 2-methylundecane thiol), and the like (for example, other commercially available thio demethylating agents), preferably tert-dodecyl mercaptan; wherein the demethylating agent is preferably present in an amount in the range of from about 2 to about 5 molar equivalents (relative to the moles of the compound of formula (V)), preferably in an amount in the range of from about 2.5 to about 4 molar equivalents; more preferably in an amount in the range of from about 2.8 to about 3.4 molar equivalents, more preferably in an amount of about 3.1 molar equivalents;

in the presence of a suitably selected base such as a suitably selected inorganic alcohol such as NaOH, KOH, LiOH, CsOH, and the like or a suitably selected alkoxide base such as NaOEt, NaOtBu, KOEt, KOtBu, LiOEt, LiOtBu, CsOEt, CsOtBu, and the like; or a suitably selected amine base such as LiNEt$_2$, NaNEt$_2$, CsNEt$_2$, LiNH$_2$, NaNH$_2$, CsNH$_2$, and the like, or a suitably selected hydride base such as NaH, KH, CsH, and the like, or a suitably selected base such as LDA, KDA, LiHMDS, KHMDS, n-BuLi, and the like; preferably NaOtBu; wherein the base is preferably present in an amount in the range of from about 2 to about 5 molar equivalents (relative to the moles of the compound of formula (V), preferably in an amount in the range of from about 2.5 to about 4 molar equivalents; more preferably in an amount in the range of from about 2.8 to about 3.4 molar equivalents, more preferably in an amount of about 3.1 molar equivalents;

in a suitably selected first organic solvent (for example a dipolar aprotic solvent) such as DMF, DMA, NMP, DMSO, sulfolane, DMI, and the like, preferably DMF; at a temperature in the range of from about 110° C. to about 150° C., preferably at a temperature in the range of 128° C. to about 135° C., more preferably at a temperature of about 131° C.; under an inert atmosphere, such as under nitrogen, under argon, under helium, and the like; to yield the corresponding compound of formula (VIII).

The compound of formula (VIII) is preferably, not isolated.

The compound of formula (VIII) is reacted with a suitably substituted compound of formula (VI), wherein $L^1$ is a suitably selected leaving group such as Br, Cl, I, mesylate, tosylate, nosylate, triflate nonaflate, and the like, preferably Br, a known compound or compound prepared by known methods;

wherein the compound of formula (VI) is preferably present in an amount greater than about 1 molar equivalent (relative to the moles of the compound of formula (V)), preferably in an amount in the range of from about 1.1 to about 2.5 molar equivalents, preferably in an amount in the range of from about 1.25 to about 1.75 molar equivalents, preferably in an amount in the range of from about 1.3 to about 1.5 molar equivalents, more preferably in an amount of about 1.4 molar equivalents;

in the presence of a suitably selected inorganic base, preferably an anhydrous inorganic base; wherein the inorganic base does not form water when reacted with or contacted with an acid, and wherein the inorganic base is sufficiently strong to neutralize any acid formed as a by-product of the reaction with the alkylating agent (for example, HBr which is formed as a by-product of the reaction with cyclopropylmethyl bromide), and wherein the inorganic base is a base which selectively does not protonate the free phenol (i.e. the phenolic OH group) on the compound of formula (VIII), such $K_2HPO_4$, anhydrous $K_3PO_4$, LiH$_2$PO$_4$, NaH$_2$PO$_4$, KH$_2$PO$_4$, CsH$_2$PO$_4$, Li$_2$HPO$_4$, Na$_2$HPO$_4$, K$_2$HPO$_4$, Cs$_2$HPO$_4$, Li$_3$PO$_4$, Na$_3$PO$_4$, K$_3$PO$_4$, Cs$_3$PO$_4$, Ca((H$_2$PO$_4$)$_2$, Ba(H$_2$PO$_4$)$_2$, Ca(HPO$_4$), Ba(HPO$_4$), Ca(PO$_4$)$_3$, Ba(PO$_4$)$_3$, and the like, preferably anhydrous K$_2$HPO$_4$ or anhydrous K$_3$PO$_4$; wherein the inorganic base is preferably present in an amount greater than about 1 molar equivalent (relative to the moles of the compound of formula (V)), preferably in an amount in the range of from about 1.5 to about 5 molar equivalents (relative to the moles of the compound of formula (V)), preferably in an amount in the range of from about 2 to about 4 molar equivalents; preferably in an amount in the range of from about 2.25 to about 3.25 molar equivalents, preferably in an amount in the range of from about 2.4 to about 3 molar equivalents;

optionally in the presence of a promoter such as NaI, NaBr, tetralkylammonium iodide (such as tetra(n-butyl) ammonium iodide, and the like), tetralkylammonium bromide (such as tetra(n-butyl)ammonium bromide, and the like), triethylbenzylammonium iodide, triethylbenzylammonium bromide, and the like; wherein the promoter is present in an amount in the range of from about 1 mole % to about 10 mole %, preferably in an amount in the range of from about 5 mole % to about 10 mole %;

in a suitably selected second organic solvent (for example a dipolar aprotic solvent) such as DMF, DMA, NMP, DMSO, sulfolane, DMI, and the like, preferably DMF; wherein the second organic solvent is preferably the same as the first organic solvent; at a temperature in the range of from about 40° C. to about 70° C., preferably at a temperature in the range of from about 55° C. to about 65° C., more preferably at a temperature of about 60° C.; to yield the corresponding compound of formula (I).

In an embodiment of the present invention, the reaction mixture containing the compound of formula (VIII), the inorganic base and the first organic solvent has a total water content of less than about 1% w/w, more preferably less than about 0.75% w/w, more preferably less than about 0.60% w/w, more preferably less than about 0.50% w/w.

In another embodiment, the present invention is directed to a process for the preparation of a compound of formula (II), as described in Scheme 3, below.

Scheme 3

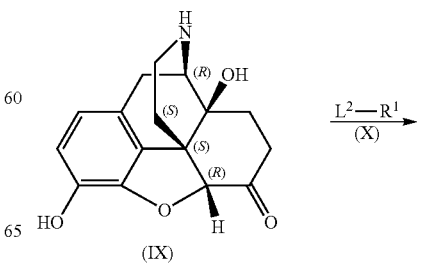

(IX)

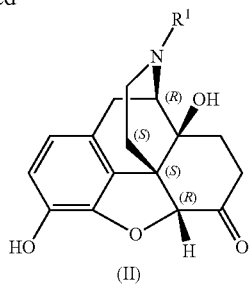

(II)

Accordingly, a suitably substituted compound of formula (IX), a known compound or compound prepared by known methods, is reacted with a suitably substituted compound of formula (X), wherein $R^1$ is selected from the group consisting of —$CH_2$-(cyclopropyl), —$CH_2$-(cyclobutyl) and —$CH_2$—CH=$CH_2$, and wherein $L^1$ is a suitably selected leaving group such as Br, Cl, I, mesylate, tosylate, nosylate, triflate nonaflate, and the like, preferably Br, a known compound or compound prepared by known methods; wherein the compound of formula (X) is preferably present in an amount greater than about 1 molar equivalent (relative to the moles of the compound of formula (IX)), preferably in an amount in the range of from about 1.1 to about 2.5 molar equivalents, preferably in an amount in the range of from about 1.25 to about 1.75 molar equivalents, preferably in an amount in the range of from about 1.3 to about 1.5 molar equivalents, more preferably in an amount of about 1.4 molar equivalents;

in the presence of a suitably selected inorganic base, preferably an anhydrous inorganic base; wherein the inorganic base does not form water when reacted with or contacted with an acid, and wherein the inorganic base is sufficiently strong to neutralize any acid formed as a by-product of the reaction with the alkylating agent (for example, HBr which is formed as a by-product of the reaction with cyclopropylmethyl bromide), and wherein the inorganic base is a base which selectively does not protonate the free phenol (i.e. the phenolic OH group) on the compound of formula (VIII), such as $K_2HPO_4$, anhydrous $K_3PO_4$, $LiH_2PO_4$, $NaH_2PO_4$, $KH_2PO_4$, $CsH_2PO_4$, $Li_2HPO_4$, $Na_2HPO_4$, $K_2HPO_4$, $Cs_2HPO_4$, $Li_3PO_4$, $Na_3PO_4$, $K_3PO_4$, $Cs_3PO_4$, $Ca((H_2PO_4)_2$, $Ba(H_2PO_4)_2$, $Ca(HPO_4)$, $Ba(HPO_4)$, $Ca(PO_4)_3$, $Ba(PO_4)_3$, and the like, preferably anhydrous $K_2HPO_4$ or anhydrous $K_3PO_4$; wherein the inorganic base is preferably present in an amount greater than about 1 molar equivalent (relative to the moles of the compound of formula (IX)), preferably in an amount in the range of from about 1.5 to about 5 molar equivalents (relative to the moles of the compound of formula (IX)), preferably in an amount in the range of from about 2 to about 4 molar equivalents; preferably in an amount in the range of from about 2.25 to about 3.25 molar equivalents, preferably in an amount in the range of from about 2.4 to about 3 molar equivalents;

optionally in the presence of a promoter such as NaI, NaBr, tetralkylammonium iodide (such as tetra(n-butyl) ammonium iodide, and the like), tetralkylammonium bromide (such as tetra(n-butyl)ammonium bromide, and the like), triethylbenzylammonium iodide, triethylbenzylammonium bromide, and the like; wherein the promoter is present in an amount in the range of from about 1 mole % to about 10 mole %, preferably in an amount in the range of from about 5 mole % to about 10 mole %;

in a suitably selected first organic solvent (for example a dipolar aprotic solvent) such as DMF, DMA, NMP, DMSO, sulfolane, DMI, and the like, preferably DMF; at a temperature in the range of from about 40° C. to about 70° C., preferably at a temperature in the range of from about 55° C. to about 65° C., more preferably at a temperature of about 60° C.; to yield the corresponding compound of formula (II).

In an embodiment of the present invention, the reaction mixture containing the compound of formula (IX), the inorganic base and the first organic solvent has a total water content of less than about 1% w/w, more preferably less than about 0.75% w/w, more preferably less than about 0.60% w/w, more preferably less than about 0.50% w/w.

In an embodiment, the present invention is directed to a process for the preparation of a compound of formula (II) wherein $R^1$ is —$CH_2$-(cyclopropyl). In another embodiment, the present invention is directed to a process for the preparation of a compound of formula (II) wherein $R^1$ is —$CH_2$—CH=$CH_2$. In another embodiment, the present invention is directed to a process for the preparation of a compound of formula (II) wherein $R^1$ is —$CH_2$-(cyclobutyl).

One skilled in the art will recognize that the compound of formula (IIc) (a compound of formula (II) wherein $R^1$ is —$CH_2$-(cyclobutyl)) corresponds to nalbuphone, an intermediate in the synthesis of the semi-synthetic opioid nalbuphine, a compound of formula (III). More particularly, as shown in the Scheme 4, below, Scheme 4

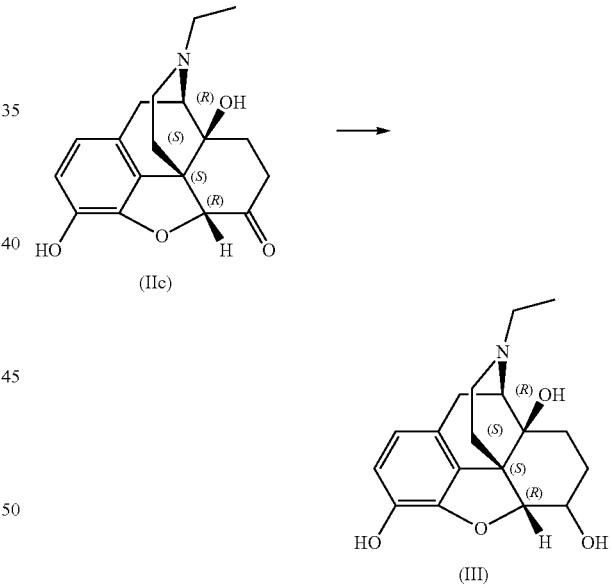

the compound of formula (IIc) may be reacted with a suitably selected reducing agent, according to known methods, for example, as described in REZAIE, R., et al., U.S. Pat. No. 8,236,957 B2, issued Aug. 7, 2012, to yield (nalbuphine) the corresponding compound of formula (III).

The present invention further comprises pharmaceutical compositions containing a product prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds or products of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 500 mg or any amount or range therein, and may be given at a dosage of from about 0.01 mg/kg/day to about 300 mg/kg/day, or any amount or range therein, preferably from about 0.01 mg/kg/day to about 50 mg/kg/day, or any amount or range therein, preferably from about 0.05 mg/kg/day to about 15 mg/kg/day, or any amount or range therein, preferably from about 0.05 mg/kg/day to about 5 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 500 mg, or any amount or range therein, preferably from about 1 mg to about 150 mg, or any amount or range therein, preferably from about 2 mg to about 50 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described in the present invention may also be carried out using a pharmaceutical composition comprising any of the products as defined herein and a pharmaceutically acceptable carrier. The pharmaceutical composition may contain between about 0.5 mg and about 500 mg of the compound, or any amount or range therein; preferably from about 1 mg to about 150 mg of the compound, or any amount or range therein, preferably from about 2 mg to about 50 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds or products of the present invention may be administered in a single daily dose, or the total daily dosage may be administered in divided doses of two, three or four times daily. Furthermore, compounds or products of the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may be formulated in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a product prepared according to any of the process(es) of the present invention, as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds or products of the present invention may be administered in any of the foregoing compositions and according to dosage regimens established in the art whenever treatment of disorders described herein is required.

The daily dosage may be varied over a wide range from about 0.01 mg to about 1,000 mg per adult human per day, or any amount or range therein. For oral administration, the compositions are preferably provided in the form of tablets containing about 0.01, 0.05, 0.1, 0.5, 1, 2.5, 4, 5, 10, 15, 25, 30, 40, 50, 60, 75, 80, 100, 150, 160, 200, 250 and 500 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day, or any amount or range therein. Preferably, the range is from about 0.05 to about 50 mg/kg of body weight per day, or any amount or range therein. More preferably, from about 0.05 to about 15 mg/kg of body weight per day, or any amount or range therein. More preferably, from about 0.05 to about 7.5 mg/kg of body weight per day, or any amount or range therein. More preferably, from about 0.05 to about 3 mg/kg of body weight per day, or any amount or range therein. The compound or product (as the active ingredient or drug) may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Synthesis Example 1

(S)-2-((4R,4aS,6R,7R,7aR,12bS)-7,9-dimethoxy-1,2,3,4,5,6,7,7a-octahydro-4a,7-ethano-4,12-methanobenzofuro[3,2-e]isoquinolin-6-yl)-3,3-dimethylbutan-2-ol

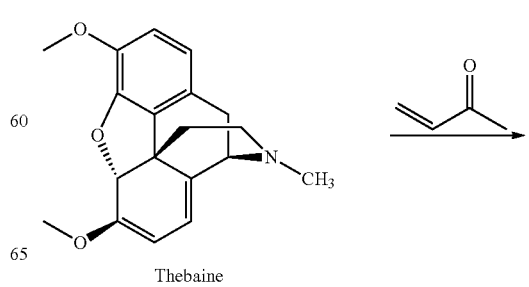

Thebaine

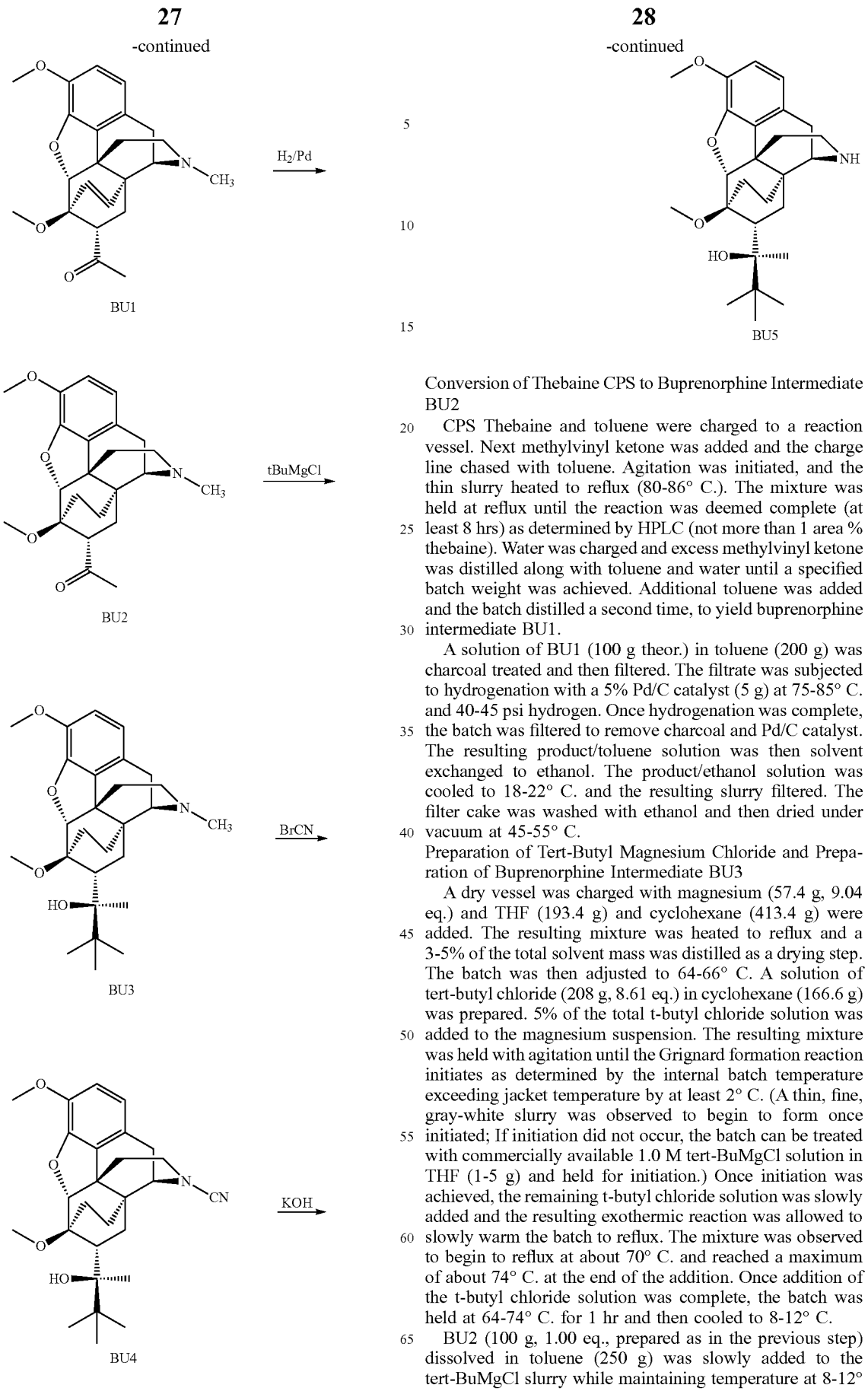

Conversion of Thebaine CPS to Buprenorphine Intermediate BU2

CPS Thebaine and toluene were charged to a reaction vessel. Next methylvinyl ketone was added and the charge line chased with toluene. Agitation was initiated, and the thin slurry heated to reflux (80-86° C.). The mixture was held at reflux until the reaction was deemed complete (at least 8 hrs) as determined by HPLC (not more than 1 area % thebaine). Water was charged and excess methylvinyl ketone was distilled along with toluene and water until a specified batch weight was achieved. Additional toluene was added and the batch distilled a second time, to yield buprenorphine intermediate BU1.

A solution of BU1 (100 g theor.) in toluene (200 g) was charcoal treated and then filtered. The filtrate was subjected to hydrogenation with a 5% Pd/C catalyst (5 g) at 75-85° C. and 40-45 psi hydrogen. Once hydrogenation was complete, the batch was filtered to remove charcoal and Pd/C catalyst. The resulting product/toluene solution was then solvent exchanged to ethanol. The product/ethanol solution was cooled to 18-22° C. and the resulting slurry filtered. The filter cake was washed with ethanol and then dried under vacuum at 45-55° C.

Preparation of Tert-Butyl Magnesium Chloride and Preparation of Buprenorphine Intermediate BU3

A dry vessel was charged with magnesium (57.4 g, 9.04 eq.) and THF (193.4 g) and cyclohexane (413.4 g) were added. The resulting mixture was heated to reflux and a 3-5% of the total solvent mass was distilled as a drying step. The batch was then adjusted to 64-66° C. A solution of tert-butyl chloride (208 g, 8.61 eq.) in cyclohexane (166.6 g) was prepared. 5% of the total t-butyl chloride solution was added to the magnesium suspension. The resulting mixture was held with agitation until the Grignard formation reaction initiates as determined by the internal batch temperature exceeding jacket temperature by at least 2° C. (A thin, fine, gray-white slurry was observed to begin to form once initiated; If initiation did not occur, the batch can be treated with commercially available 1.0 M tert-BuMgCl solution in THF (1-5 g) and held for initiation.) Once initiation was achieved, the remaining t-butyl chloride solution was slowly added and the resulting exothermic reaction was allowed to slowly warm the batch to reflux. The mixture was observed to begin to reflux at about 70° C. and reached a maximum of about 74° C. at the end of the addition. Once addition of the t-butyl chloride solution was complete, the batch was held at 64-74° C. for 1 hr and then cooled to 8-12° C.

BU2 (100 g, 1.00 eq., prepared as in the previous step) dissolved in toluene (250 g) was slowly added to the tert-BuMgCl slurry while maintaining temperature at 8-12°

C. Once addition was complete, the mixture was held at 0-12° C. for 1 hr, then transferred into a quench vessel containing ammonium chloride (417 g, 29.90 eq.) solution in water (1733 g). The transfer was exothermic and the quench vessel internal temperature was maintained at 0-40° C. (to ensure isobutane gas remains in solution). Once the quench was complete the mixture is held at 20-30° C. with agitation for six hours to consume any un-reacted magnesium chips. Next the batch was settled and the lower aqueous layer separated and discarded. An aqueous phosphate buffer was prepared by combining water (1326 g), 85% phosphoric acid (127.4 g) and 28-30% ammonium hydroxide (59.4 g). The pH of the buffer was adjusted to 3.8-4.0 with phosphoric acid and/or ammonium hydroxide. The organic layer was washed twice with the buffer (each wash is ½ total buffer volume), then once with water (200 g) to yield buprenorphine intermediate BU3.

Preparation of Buprenorphine Intermediate BU4

BU3 (100 g, prepared as in the previous step), sodium carbonate (5.0 g) and DCM (200 g) were combined in a reaction vessel and the temperature of the resulting mixture adjusted to 20° C. A 50 wt % solution of cyanogen bromide in DCM was added and the resulting mixture held at 22° C. for 22 hrs.

The resulting BU4 containing reaction mixture (100 g BU3 scale) was quenched by addition of water (68 g), ethanol (80 g) and ammonium hydroxide 28-30% (72.5 g). The resulting mixture was settled and the lower product containing layer combined with water (160 g) and ethanol (80 g). The mixture was settled again and the lower product containing DCM layer separated. The DCM solvent was then exchanged to ethanol by charging ethanol and distilling the batch to 75° C. to yield a solution of buprenorphine intermediate BU4 in ethanol.

Preparation of Buprenorphine Intermediate 5

The BU4/ethanol solution (prepared as in the previous step) was combined with diethylene glycol (100 g BU3) and then 45% aq. KOH was added (71 g). The resulting mixture was distilled until batch temperature reached 130° C. The mixture was then held at 130° C. for 4 hrs and sampled for reaction completion.

After reaching completion, the mixture containing BU5 (100 g BU3 scale) was cooled to 50° C. Toluene (200 g) and water (50 g) were added and the mixture warmed to 50° C. The mixture was allowed to settle, and the bottom layer separated. The bottom layer was combined with toluene (100 g) and water (50 g). The mixture was adjusted to 50° C. and allowed to settle. The bottom layer was separated and combined with a third portion of toluene (100 g) and warmed to 50° C. The mixture was settled and the bottom diethyleneglycol/water layer separated and discarded. The three toluene extracts were combined and water washed twice (2×100 g/each). The toluene layers were then reduced by vacuum distillation to approximately ⅔ the original volume. The resulting solution was then polish filtered to remove trace insoluble material. Heptanes (120 g) were added and the mixture was heated to dissolve the solids. The solution as cooled to −10° C. and the resulting crystalline solid collected by filtration and dried under vacuum at 50° C. to yield buprenorphine intermediate BU5 (also known as of (4R,4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-ol).

Synthesis Example 2

Preparation of (4R,4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-ol

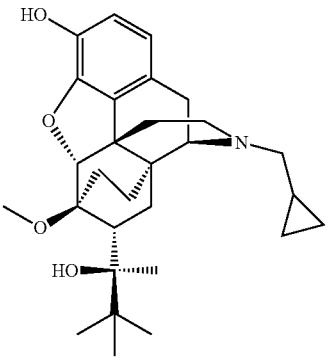 [SMILES: CO[C@@]12CC[C@@]3(C[C@@H]1[C@](C)(O)C(C)(C)C)[C@H]1Cc4ccc(O)c5c4[C@@]3(CCN1CC1CC1)[C@H]2O5]

Step A

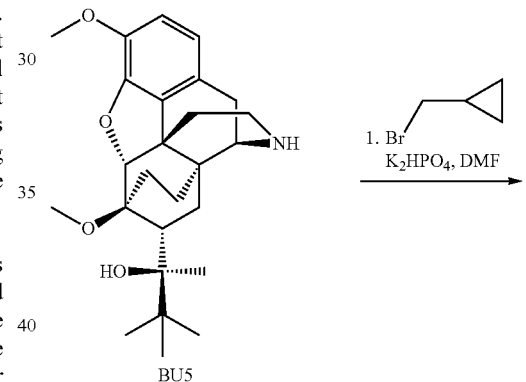

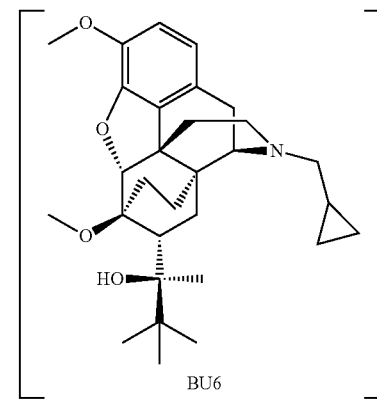

A 150 mL 5-neck EasyMax vessel was charged with DMF (56.6 g, 60 mL), which was then purged with $N_2$. Anhydrous $K_2HPO_4$ (20.6 g) was added and the resulting mixture stirred under $N_2$ at 20-25° C. for 5-10 min. To the mixture was then added BU5 (20.2 g) and cyclopropylmethyl bromide (8.84 g), and the resulting mixture heated to 55° C., stirring for 6.5 hours. The mixture was sampled and progression measured by HPLC. The reaction was deemed complete when the area % of starting material (BU5) was less than 0.15% A.

Measured HPLC:
BU5: 0.12 area %; BU6: 98.99 area %

The mixture was then heated to 70° C. and stirred for 30 minutes. The resulting mixture was then filtered at 70° C. and the filter cake washed with DMF (38 g, 40 mL) at 65-75° C. The filtrate was cooled to room temperature and used in the next step directly.

Step B

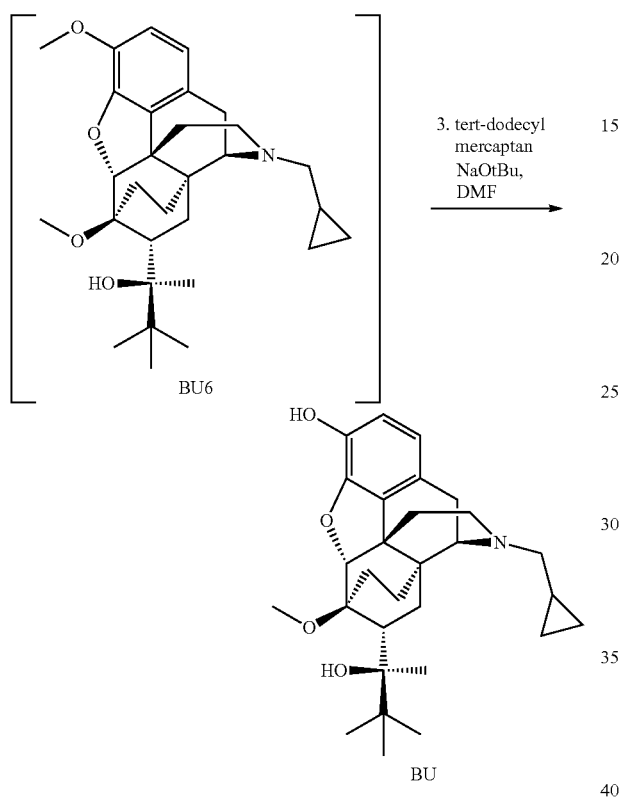

To the filtrate prepared in STEP A above was added tert-dodecyl mercaptan (29.7 g) at room temperature and the resulting mixture stirred under $N_2$ atmosphere. Sodium tert-butoxide (14.4 g) was then added to the mixture as a solid in one portion. The resulting opalescent solution was heated over 1 hour to 135° C. and a first portion of tert-butanol was distilled off under an inert atmosphere. The resulting mixture was stirred for 2 hours 10 min at 135° C. and distillation under $N_2$ continued. The mixture was sampled and progression measured by HPLC. The reaction was deemed complete when the area % of starting material (BU5) was less than 0.15% A. The resulting mixture was cooled to 50° C. over 1 hour.

Measured HPLC:
BU6: 2.18 area %; BU: 92.67 area %

HPLC Method:

The following parameters were used in the HPLC method noted above. Variant HPLC System with pump module 9012, detector module 9050 and autosampler 9300. The column was an X-Bridge, C8, 3.5 mm, 1150 mm×4.6 mm. injection volume was 10 µl, flow rate was 1.0 mL/min, equilibration time was 5 min, temperature was 40° C. and detection was at 284 nm. Solvent A was prepared by mixing ammonium acetate (5.0 g) in water (900 m mL), adjusting the pH of the solution to pH 5.0 with glacial acetic acid and bringing the mixture to volume by addition of water. Solvent B was prepared by mixing 50% acetic acid (0.5 mL) with sufficient methanol to attain a final volume of 1000 mL). The gradient was as follows:

| t (min) | % A | % B |
| --- | --- | --- |
| 0 | 70 | 30 |
| 15 | 40 | 60 |
| 25 | 40 | 60 |
| 55 | 40 | 60 |
| 55 | 5 | 95 |

Synthesis Example 3

Preparation of (4R,4aS,6R,7R,7aR,12bS)-3-(cyclopropylmethyl)-6-((S)-2-hydroxy-3,3-dimethylbutan-2-yl)-7-methoxy-1,2,3,4,5,6,7,7a-octahydro-4a,7-ethano-4,12-methanobenzofuro[3,2-e]isoquinolin-9-ol Hydrochloride Salt

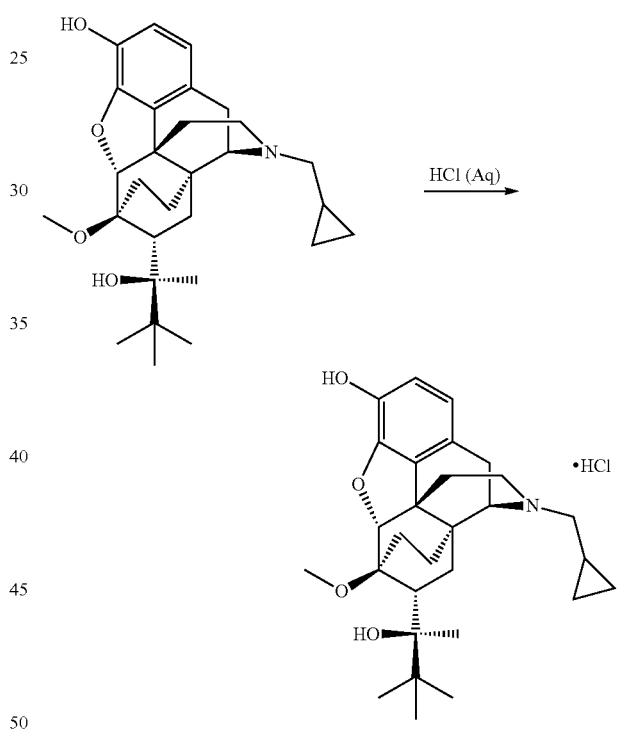

The following example describes a recipe/procedure for the synthesis of buprenorphine HCl. At least one batch of buprenorphine HCl was prepared according to said recipe/procedure, and the product isolated as a white to off-white crystalline powder.

A glass lined reactor vessel was purged with $N_2$. To the reactor was then added a suspension of BU in 2-propanol (approximately 22.9 g per 100 g solvent) and the resulting mixture heated to 70° C. to complete dissolution. A small portion of HCl was added and the resulting solution seeded with Bu HCl. After stirring for one hour at 70° C., a second portion of HCl was added at 70° C., over 3-5 hours. The total amount of HCl was 1.05 M/M. The suspension was then cooled via the following non-linear cooling curve to a final temperature of 0° C.: Step A: cooling to 57° C., over 2 hours; Step B: cooling to 42° C., over 2 hours; Step C: cooling to 23° C., over 2 hours; and Step D: cooling to 0° C., over 2 hours. The resulting suspension was filtered and the solid dried to yield the title compound.

Synthesis Example 4

Preparation of (4R,4aS,7aR,12bS)-3-allyl-4a,9-dihydroxy-2,3,4,4a,5,6-hexahydro-1H-4,12-methanobenzofuro[3,2-e]isoquinolin-7(7aH)-one

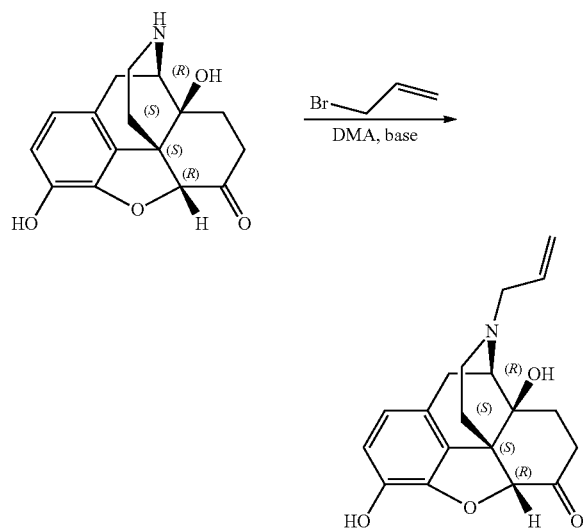

Noroxymorphone (NOMO) was converted to naloxone by reacting with allylbromide in N,N-dimethylacetamide (DMA) in the presence of dipotassium hydrogenphosphate.

Noroxymorphone (4.0 g) was suspended in DMA (7.05 g, 1.75 mass eq.) at 20-30° C. To the reaction mixture was then added allybromide (1.68 g, 1.0 mol. eq.). The resulting suspension was stirred at 20-30° C. for 60-70 min until a clear brown solution was formed. To the mixture was then added dipotassium hydrogenphosphate (2.43 g, 1 mol. eq.) at 20-30° C. The reaction mixture was stirred at 20-30° C. for 12 h. During the stirring a slightly turbid suspension was formed. The reaction conversion was monitored by HPLC (R&D, area-%), with IPC after 12 h at 20-30° C.: noroxymorphone: 0.2%, naloxone: 98.0%, 3-allyl-naltrexone: 0.4%).

Note: water content of $K_2HPO_4$ was 2.2 wt %, KF

Synthesis Example 5

Preparation of (4R,4aS,7aR,12bS)-3-(cyclopropylmethyl)-4a,9-dihydroxy-2,3,4,4a,5,6-hexahydro-1H-4,12-methanobenzofuro[3,2-e]isoquinolin-7(7aH)-one

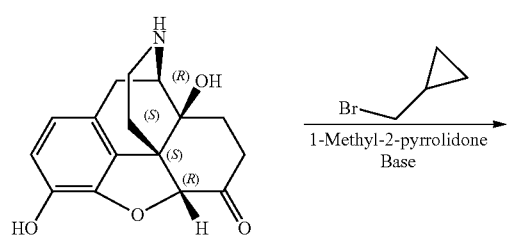

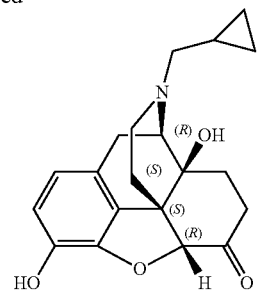

Noroxymorphone (NOMO) was converted to naltrexone, reacting with bromomethylcyclopropane in 1-methyl-2-pyrrolidone (NMP) in the presence of a base. In this work two different bases were investigated: sodium carbonate and dipotassium hydrogenphosphate. Additionally, reaction time and temperature were also varied. Table 1, below list experimental conditions for the completed experiments.

TABLE 1

| Experimental Conditions | | | | |
|---|---|---|---|---|
| Experiment ID No. | Time and Temperature | Base | Mol. Eq. (base) | Mass Eq. (NMP) |
| 107-01 | 2.5 h 80° C. | $Na_2CO_3$ | 1.1 | 1.4 |
| 107-02 | 5.5 h 80° C. | $Na_2CO_3$ | 1.1 | 1.4 |
| 107-03 | +1.5 h 85° C. | $Na_2CO_3$ | 1.1 | 1.4 |
| 108-01 | 2.5 h 80° C. | $K_2HPO_4$[1] | 1.1 | 1.4 |
| 108-02 | 5.5 h 80° C. | $K_2HPO_4$[1] | 1.1 | 1.4 |
| 108-03 | +1.5 h 85° C. | $K_2HPO_4$[1] | 1.1 | 1.4 |
| 110-01 | 5 h 80° C. | $K_2HPO_4$[2] | 1.1 | 1.4 |
| 110-02 | 7 h 80° C. | $K_2HPO_4$[2] | 1.1 | 1.4 |
| 111-01 | 5 h 80° C. | $K_2HPO_4$[2] | 2.0 | 2.1 |
| 111-02 | 7 h 80° C. | $K_2HPO_4$[2] | 2.0 | 2.1 |
| 112-01 | 5 h 80° C. | $K_2HPO_4$[2] | 3.0 | 2.8 |
| 112-02 | 7 h 80° C. | $K_2HPO_4$[2] | 3.0 | 2.8 |

[1]Water content of $K_2HPO_4$ = 2.2 wt-%, KF
[2]Water content of $K_2HPO_4$ = 0.6 wt-%, KF Sodium Carbonate To 1-methyl-2-pyrrolidone (NMP) (7.1 g) were added noroxymorphone (5.0 g) and sodium carbonate (2.0 g, 1.1 mol. eq.) at 20-25° C. After inerting with nitrogen, bromomethyl-cyclopropane (2.7 g) was added dropwise, and the dropping funnel washed with 1-methyl-2-pyrrolidone (1.5 g). The reaction mixture was heated to 80° C. during 1 h and stirred at 80° C. for 5.5 h. The temperature was increased to 85° C. and the reaction mixture held for 1.5 h. The reaction conversion was monitored by HPLC (R&D, area-%) with IPC as shown in Table 2.

Dipotassium Hydrogenphosphate

To 1-methyl-2-pyrrolidone (NMP) (7.1 g) were added noroxymorphone (2.5 g) anddipotassium hydrogenphosphate (in amounts as noted in Table 1 above) at 20-25° C. After inerting with nitrogen, bromomethyl-cyclopropane (1.4 g) was added dropwise, and the dropping funnel washed with 1-methyl-2-pyrrolidone (0.75 g). The reaction mixture was heated to 80° C. during 1 h and stirred at 80° C. for 5.5 h. The temperature was increased to 85° C. and the reaction mixture held for 1.5 h. The reaction conversion was monitored by HPLC (R&D, area-%) with IPC as shown in Table 2.

TABLE 2

| Reaction Products (HPLC Area %) | | | |
|---|---|---|---|
| Experiment ID No. | NOMO area-%, HPLC | Naltrexone area-%, HPLC | Impurity[3] area-%, HPLC |
| 107-01 | 1.9 | 93.9 | 3.0 |
| 107-02 | 1.3 | 92.0 | 5.6 |
| 107-03 | 1.1 | 90.9 | 6.3 |
| 108-01 | 18.0 | 80.5 | 0.3 |
| 108-02 | 11.4 | 86.8 | 0.5 |
| 108-03 | 8.5 | 89.5 | 0.6 |
| 110-01 | 2.3 | 96.0 | 0.6 |
| 110-02 | 2.1 | 96.1 | 0.9 |
| 111-01 | 1.7 | 96.5 | 0.6 |
| 111-02 | 1.6 | 96.5 | 0.9 |
| 112-01 | 1.5 | 97.0 | 0.4 |
| 112-02 | 1.4 | 96.9 | 0.7 |

[3]3-(cyclopropylmethyl)-naltrexone

In summary, the use of $Na_2CO_3$ was observed to result in the fastest conversion, but also the highest impurity ratio. The conversion with $K_2HPO_4$ was observed to be slower. However, compared with $Na_2CO_3$ the use of $K_2HPO_4$ as the base resulted in a lower ratio of the undesired dialkylated impurity. If dried $K_2HPO_4$ was used, the reaction was observed to run to near completion. A higher amount of $K_2HPO_4$ was also observed to result in better conversion, although the reaction mixture needed to be diluted, to have a stirrable reaction mixture.

Formulation Example 1

Solid, Oral Dosage Form—Prophetic Example

As a specific embodiment of an oral composition, 100 mg of the compound prepared as in Example 3 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of a compound of formula (I)

(I)

or a pharmaceutically acceptable salt thereof; comprising

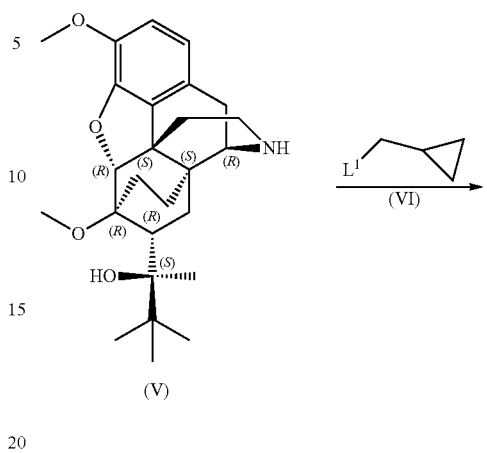

(V)

(VI)

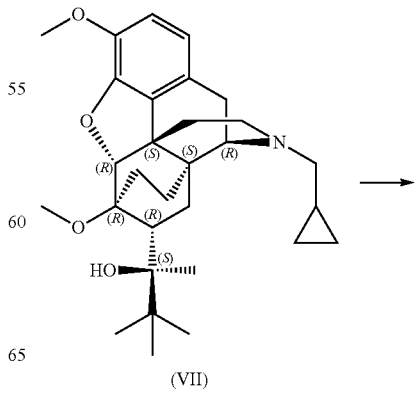

(VII)

reacting a compound of formula (V) with a compound of formula (VI), wherein $L^1$ is a leaving group; in the presence of an inorganic base; wherein the inorganic base does not form water when reacted with or contacted with an acid; in a first organic solvent; at a temperature in the range of from about 40° C. to about 70° C.; to yield the corresponding compound of formula (VII); and (VII)

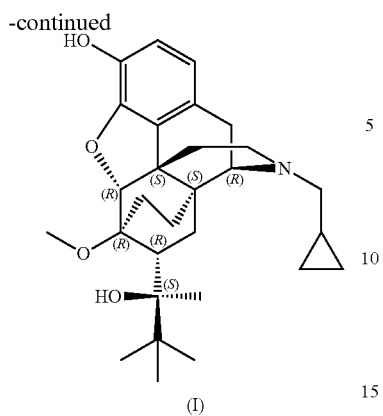

(I)

reacting the compound of formula (VII) with a demethylating agent; in the presence of a base; in a second organic solvent; at a temperature in the range of from about 110° C. to about 150° C.; under an inert atmosphere; to yield the corresponding compound of formula (I).

2. A process as in claim 1, wherein $L^1$ is bromo.

3. A process as in claim 1, wherein the compound of formula (VI) is present in an amount in the range of from about 1.1 to about 2.5 molar equivalents.

4. A process as in claim 1, wherein the compound of formula (VI) is present in an amount in the range of from about 1.25 to about 1.75 molar equivalents.

5. A process as in claim 1, wherein the inorganic base is an anhydrous inorganic base.

6. A process as in claim 1, wherein the inorganic base is anhydrous $K_2HPO_4$.

7. A process as in claim 1, wherein the inorganic base is present in an amount in the range of from about 2 to about 4 molar equivalents.

8. A process as in claim 1, wherein the inorganic base is present in an amount of in the range of from about 2.25 to about 3.25 molar equivalents.

9. A process as in claim 1, wherein the first organic solvent is DMF.

10. A process as in claim 1, wherein the compound of formula (VII) is not isolated.

11. A process as in claim 1, wherein the demethylating agent is tert-dodecyl mercaptan and wherein the base is an alkoxide base.

12. A process as in claim 10, wherein the alkoxide base is NaOtBu.

13. A process as in claim 1, wherein the demethylating agent is present in an amount in the range of from about 2.5 to about 4 molar equivalents.

14. A process as in claim 1, wherein the demethylating is present in an amount of in the range of from about 2.8 to about 3.4 molar equivalents.

15. A process as in claim 1, wherein the base is present in an amount in the range of from about 2.5 to about 4 molar equivalents.

16. A process as in claim 1, wherein the base is present in an amount of in the range of from about 2.8 to about 3.4 molar equivalents.

17. A process as in claim 1, wherein the compound of formula (V) is reacted with the compound (VI) in the presence of a promoter.

18. A process as in claim 17, wherein the promoter is NaI; and wherein the NaI is present in an amount in the range of from about 5 mole % to about 10 mole %.

19. A process as in claim 1, further comprising reacting the compound of formula (I) with HCl to yield the corresponding hydrochloride salt of the compound of formula (I).

20. A process for the preparation of a compound of formula (I)

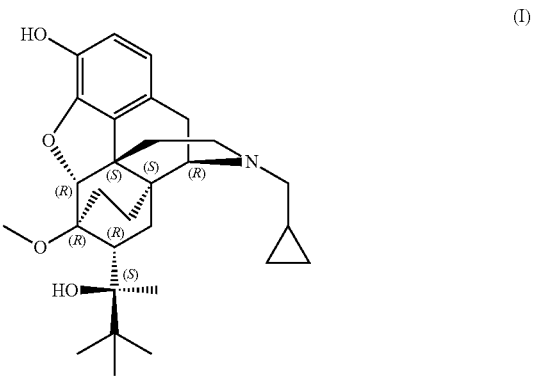

or a pharmaceutically acceptable salt thereof; comprising

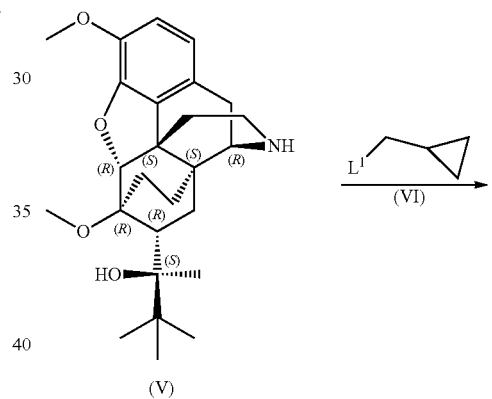

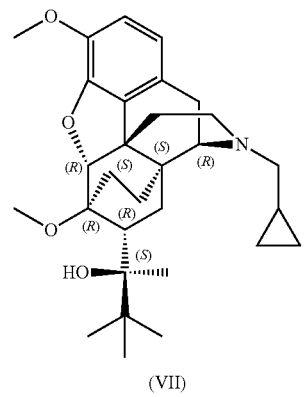

reacting a compound of formula (V) with a compound of formula (VI), wherein $L^1$ is bromo; wherein the compound of formula (VI) is present in an amount of about 1.4 molar equivalents;

in the presence of anhydrous $K_2HPO_4$; wherein the anhydrous $K_2HPO_4$ is present in an amount of in the range of from about 2.4 to about 3 molar equivalents;

in DMF; at a temperature of about 60° C.; to yield the corresponding compound of formula (VII); and

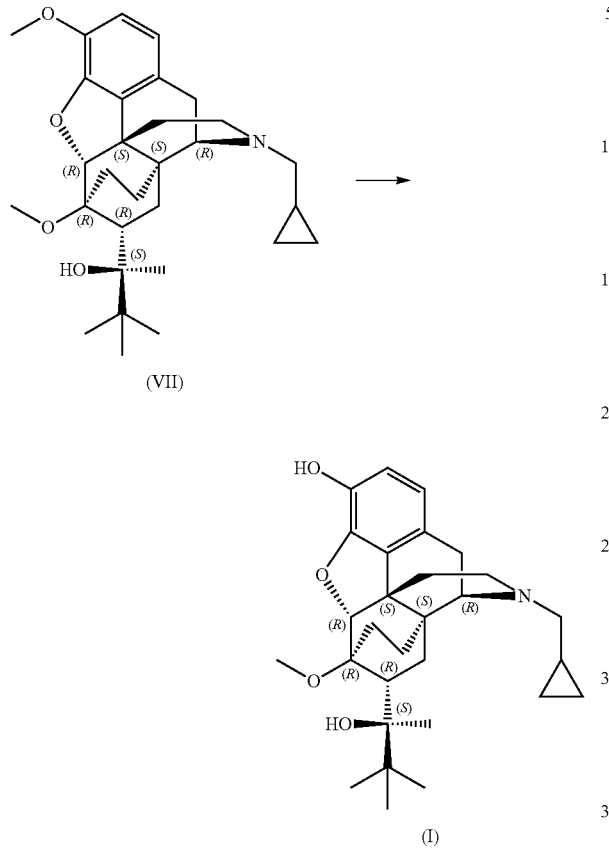

reacting the compound of formula (VII) with tert-dodecylmercaptan; wherein the tert-dodecyl mercaptan is present in an amount of about 3.1 molar equivalents; in the presence of NaOtBu; wherein the NaOtBu is present in amount of about 3.1 molar equivalents;

in DMF; at a temperature of about 131° C.; under an inert atmosphere; to yield the corresponding compound of formula (I).

21. A process for the preparation of a compound of formula (VII)

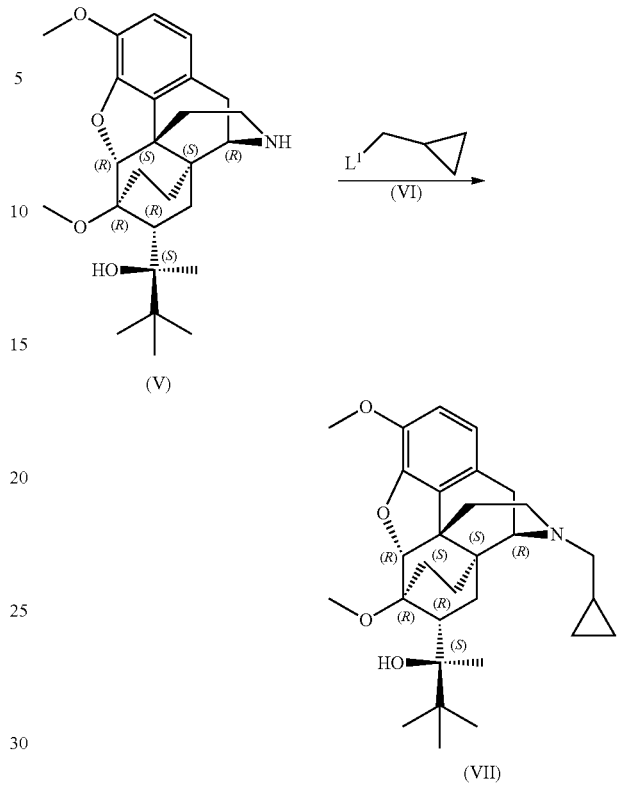

or a pharmaceutically acceptable salt thereof; comprising reacting a compound of formula (V) with a compound of formula (VI), wherein L¹ is a leaving group; in the presence of an inorganic base; wherein the inorganic base does not form water when reacted with or contacted with an acid; in a first organic solvent; at a temperature in the range of from about 40° C. to about 70° C.; to yield the corresponding compound of formula (VII).

22. A process as in claim 21, wherein L¹ is bromo; wherein the compound of formula (VI) is present in an amount of about 1.4 molar equivalents; wherein the inorganic base is anhydrous K₂HPO₄; wherein the anhydrous K₂HPO₄ is present in an amount of in the range of from about 2.4 to about 3 molar equivalents; wherein the first organic solvent is DMF; and wherein the compound of formula (V) is reacted with the compound of formula (VI) at a temperature of about 60° C.

23. A process as in claim 21, further comprising

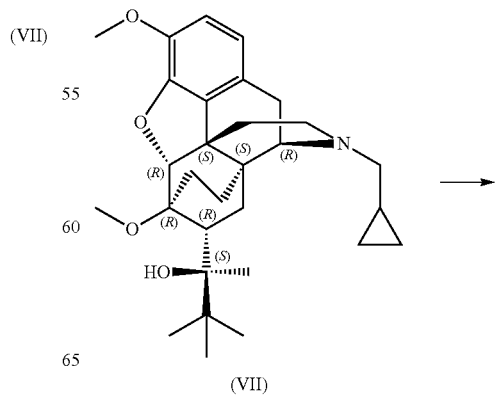

-continued

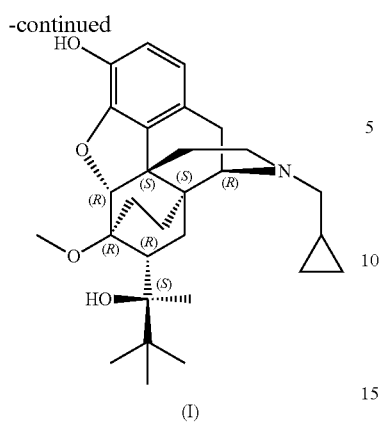

(I)

reacting the compound of formula (VII) with a demethylating agent; in the presence of a base; in a second organic solvent; at a temperature in the range of from about 110° C. to about 150° C.; under an inert atmosphere; yield the corresponding compound of formula (I).

24. A process for the preparation of a compound of formula (I)

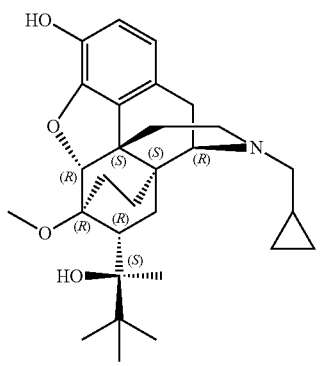

or a pharmaceutically acceptable salt thereof; comprising

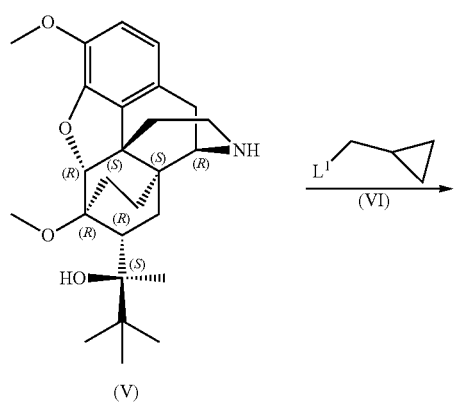

-continued

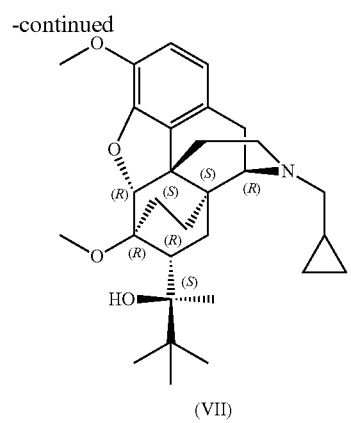

(VII)

reacting a compound of formula (V) with a compound of formula (VI), wherein L1 is a leaving group; in the presence of an inorganic base; wherein the inorganic base does not form water when reacted with or contacted with an acid; in a first organic solvent; at a temperature in the range of from about 40° C. to about 70° C.; to yield the corresponding compound of formula (VII); and

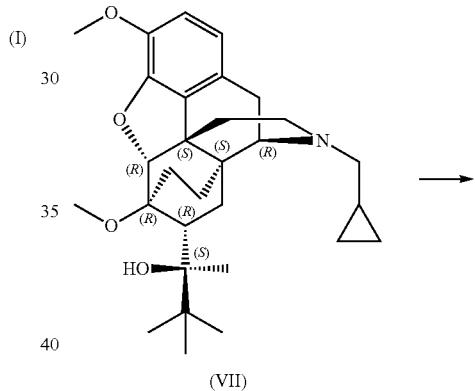

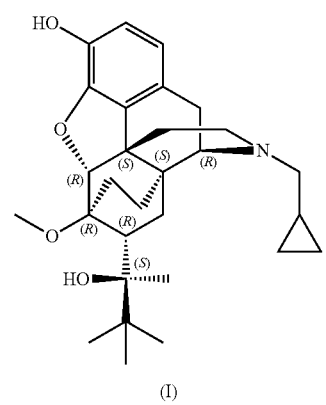

(I)

reacting the compound of formula (VII) with a demethylating agent to yield the corresponding compound of formula (I).

* * * * *